US012667266B1

(12) United States Patent
Wang et al.

(10) Patent No.: US 12,667,266 B1
(45) Date of Patent: Jun. 30, 2026

(54) ACCURATE CONTINUOUS BLOOD PRESSURE MEASUREMENT DEVICE

(71) Applicant: Sharon Xiaorong Wang, Rancho Santa Margarita, CA (US)

(72) Inventors: Sharon Xiaorong Wang, Rancho Santa Margarita, CA (US); Jason Andrew Chen, Boston, MA (US); William Barry Chen-Mertens, Redondo Beach, CA (US)

(73) Assignee: JB HealthTech, Rancho Santa Margarita, CA (US)

( * ) Notice: Subject to any disclaimer, the term of this patent is extended or adjusted under 35 U.S.C. 154(b) by 0 days.

(21) Appl. No.: 19/171,314

(22) Filed: Apr. 6, 2025

(51) Int. Cl.
*A61B 5/021* (2006.01)
*A61B 5/00* (2006.01)
*A61B 5/0235* (2006.01)

(52) U.S. Cl.
CPC ........ *A61B 5/02141* (2013.01); *A61B 5/0235* (2013.01); *A61B 5/6829* (2013.01)

(58) Field of Classification Search
CPC .. A61B 5/02141; A61B 5/0235; A61B 5/6829
See application file for complete search history.

(56) References Cited

U.S. PATENT DOCUMENTS

| | | | |
|---|---|---|---|
| 4,539,997 | A | 9/1985 | Wesseling et al. |
| 5,105,138 | A | 4/1992 | Hiroi |
| 2009/0163823 | A1 | 6/2009 | Takahashi et al. |
| 2010/0069764 | A1 | 3/2010 | Kang |
| 2011/0105917 | A1 | 5/2011 | Fortin et al. |
| 2013/0023778 | A1 | 1/2013 | Sawanoi et al. |
| 2015/0201852 | A1 | 7/2015 | Fortin |
| 2016/0310149 | A1 | 10/2016 | Downey |
| 2017/0215749 | A1 | 8/2017 | Zhuo et al. |
| 2018/0103856 | A1 | 4/2018 | Murray et al. |
| 2019/0110694 | A1 | 4/2019 | Jian et al. |
| 2019/0261872 | A1 | 8/2019 | Axelrod et al. |
| 2021/0204824 | A1 | 7/2021 | Wang et al. |

FOREIGN PATENT DOCUMENTS

| | | | | |
|---|---|---|---|---|
| JP | 3687707 B2 | * | 8/2005 | ............. A61B 5/022 |
| WO | WO-2021247300 A1 | * | 12/2021 | ......... A61B 5/02225 |

* cited by examiner

*Primary Examiner* — Navin Natnithithadha

(57) ABSTRACT

A continuous blood pressure measurement device includes a cuff airbag pneumatically connected to an inflation/deflation unit and a pressure detection unit. The device also comprises at least one light-emitting diode, at least one photodiode, and a volume detection unit configured to convert photoplethysmogram signals into arterial volume signals. A control unit precisely tracks a predefined setpoint to achieve arterial unloading based on a volume compensation method. An extraction unit reconstructs a high-fidelity arterial blood pressure waveform and accurately determines systolic, diastolic, mean arterial pressures, and heart rate.

18 Claims, 13 Drawing Sheets

| Unit = mmHg | Mean Error | Standard Deviation |
|---|---|---|
| Systolic | 0.02 | 3.33 |
| Diastolic | 1.34 | 3.37 |

ACCURATE CONTINUOUS BLOOD PRESSURE MEASUREMENT DEVICE

BACKGROUND

Field of the Invention

The present invention relates to continuous blood pressure monitoring systems. More specifically, it pertains to a device, control method, and signal extraction method for continuous blood pressure measurement based on a volume compensation technique.

Description of the Related Art

Blood pressure (BP) measurement is a critical component of vital sign monitoring, particularly in critically ill patients. Conventional brachial cuff oscillometric devices (BCODs), while widely used, often yield inaccurate readings in individuals with hypertension, hypotension, or arrhythmias such as atrial fibrillation.[1,2] A meta-analysis by Picone et al. comparing intra-arterial and cuff-based brachial BP measurements reported that cuff-based methods tend to underestimate systolic pressure by approximately 6 mmHg and overestimate diastolic pressure by a similar amount, resulting in an underestimation of pulse pressure by roughly 12 mmHg.[1] Furthermore, a study by Wax et al. indicated that in extreme cases, measurement errors may reach up to 38 mmHg[2]—particularly in patients with abnormal blood pressure conditions, where accuracy is clinically essential.

The gold standard for arterial blood pressure measurement is the intra-arterial catheter, commonly referred to as an arterial line (A-line). In this method, a pressure transducer is placed in direct contact with the bloodstream via a catheter, enabling highly accurate and continuous measurement of arterial pressure. This approach is often described as "direct measurement." Analogous to measuring the length of a table with a ruler placed at its edge, the pressure transducer functions like a ruler directly aligned with the subject of measurement. Because the transducer resides within the catheter and maintains direct interface with the blood, it offers precise and reliable readings, akin to a ruler permanently affixed to the edge of the table.

In contrast to direct intra-arterial measurement, oscillometric (OSC) methods estimate blood pressure by applying counterpressure to the artery through an inflatable cuff that is pneumatically connected to a pressure sensor. This setup functions analogously to using an external ruler to estimate length. However, because the relationship between cuff pressure and true arterial pressure is not directly measurable, OSC devices rely on signal analysis and empirically derived algorithms to estimate systolic and diastolic pressures. These algorithms are typically based on population-level statistical models and do not account for individual physiological variability. As a result, measurement inaccuracies are common, particularly in patients who are underrepresented in the data sets used to calibrate these models. This process is akin to using a ruler without "eyes" for visual feedback—attempting to measure the edge of a table indirectly and without precision.

In recent years, substantial efforts have been directed toward the development of cuffless blood pressure measurement technologies. Many of these systems utilize photoplethysmogram (PPG) signals in combination with electrocardiogram (ECG) data to compute pulse arrival time (PAT) or pulse transit time (PTT)[3-4] as surrogate indicators of blood pressure. Other emerging approaches involve thin-film sensors designed to measure skin capacitance.[5-6] By eliminating the need for mechanical cuff inflation and deflation, cuffless methods offer improved patient comfort and convenience, and represent a promising alternative to conventional techniques. However, in the absence of an external pressure reference as the "ruler", such systems must estimate blood pressure indirectly by converting sensor signals into pressure values-a process that introduces additional complexity and potential inaccuracy when compared to pressure-based methods using a physical cuff.

Research has demonstrated a significant negative correlation between PTT and systolic blood pressure,[7-9] thereby limiting the reliability of direct estimation methods based on this parameter. To enhance accuracy, machine learning techniques have been applied, utilizing population-based statistical models. However, such approaches conflict with a foundational principle of sensing: that an individual physiological measurement cannot be precisely derived from generalized population data. These models often fail to account for individuals at the extremes of the blood pressure range, leading to underfitting in cases of severe hypertension or hypotension, and overfitting during patient monitoring. Consequently, measurement errors increase, typically manifesting as underestimation of systolic pressure in hypertensive patients and overestimation in hypotensive individuals—introducing the highest level of risk to the most clinically vulnerable populations.

Most cuffless blood pressure measurement devices require initial calibration prior to clinical use. This calibration process typically involves inputting reference systolic and diastolic pressure values obtained from A-lines or BCODs. A software-based linear transformation is then applied to convert sensor data into estimated blood pressure readings. However, the dependence on external device calibration significantly limits the practicality of cuffless systems in certain clinical environments, such as neonatal intensive care units (NICUs), where A-lines may not be feasible and BCOD measurements are known to be even less accurate in neonates than in adults.

U.S. Pat. No. 4,539,997 to Wesseling et al. discloses a continuous blood pressure monitoring system comprising a PPG sensor integrated into a finger-mounted air cuff, which is often referred as volume compensation. This system combines the PPG sensor with a conventional inflation/deflation mechanism and a pressure sensor, similar to those used in OSC devices. Wesseling et al. established a relationship between the PPG signal and arterial volume, demonstrating that when the PPG signal is maintained at the arterial unload point—defined as the point where transmural pressure is zero—the external cuff pressure equals the internal arterial pressure. This allows for continuous, non-invasive measurement of blood pressure. Using the earlier table-measurement analogy, the PPG sensor functions as an "eye" that aligns the edge of the table with the "ruler", offering an indirect yet potentially highly accurate method of measurement.

However, the relationship between the PPG signal and arterial pressure is patient-specific and varies significantly across individuals. Without a systematic method to determine and apply this individualized relationship, the accuracy of the Wesseling et al. system is limited and actually perform worse than conventional oscillometric devices. In the table-measurement analogy, this is akin to using an "eye" that views the "ruler" at an angle, resulting in parallax error and inaccurate measurements. Furthermore, sustained application of high pressure to the fingers can impair local blood circulation, leading to symptoms such as discoloration (commonly referred to as "purple finger") and numbness. While the system presents the benefit of continuous monitoring, its limited accuracy and associated physiological side effects have posed barriers to widespread clinical adoption.

SUMMARY

The present invention provides an accurate, continuous blood pressure measurement device (hereinafter referred to as the Device). The Device addresses the limitations of existing volume compensation methods and achieves high accuracy of 3±5 mmHg (mean error±standard deviation) with continuous monitoring, making it particularly suitable for critically ill patients in hospital settings. It establishes an individualized relationship between arterial volume and pressure for each subject, enabling precise, continuous, and noninvasive monitoring. Returning to the earlier table measurement analogy, the invention integrates not only a "ruler" and an "eye" but also the capability to align them correctly—effectively enabling a true indirect measurement of blood pressure. Furthermore, the system employs an extraction method that applies a reduced counterpressure to the finger, thereby mitigating circulation issues such as discoloration ("purple finger") and improving user comfort. The invention aims to serve as a noninvasive alternative to intra-arterial catheter systems currently used for continuous blood pressure monitoring.

In one or more embodiments of the present invention, an accurate continuous blood pressure measurement device based on a volume compensation method comprises: a cuff configured to compress an artery at a designated measurement site; an inflation/deflation unit for regulating the internal pressure of the cuff; a pressure detection unit for detecting the cuff pressure; a volume detection unit for acquiring an arterial volume signal indicative of the arterial volume per unit length; a control unit configured to regulate cuff pressure by controlling the inflation/deflation unit in response to the arterial volume signal; and an extraction unit configured to continuously extract and reconstruct the arterial pressure waveform. The extraction unit further calculates systolic pressure, diastolic pressure, mean arterial pressure, and heart rate on a beat-by-beat basis.

In one or more embodiments of the present invention, a control unit is provided to regulate the inflation/deflation unit in order to maintain the artery in an unloaded state, in accordance with a volume compensation method. The control unit employs a model-based predictive feedback servo design for volume regulation, enabling accurate tracking of a prescribed controller setpoint. This configuration allows for precise control of cuff pressure in real time, enhancing the fidelity of arterial pressure measurement.

In one or more embodiments of the present invention, an extraction unit is provided to detect heartbeats within the pressure waveform based on a volume compensation method. Using this information, the extraction unit calculates systolic pressure, diastolic pressure, mean arterial pressure, and heart rate. In embodiments where the volume setpoint corresponds to a pressure below the mean arterial pressure, the extraction unit is further configured to reconstruct the true arterial pressure waveform. This approach enhances patient comfort by allowing the application of lower counterpressure, thereby supporting safe and effective long-term continuous monitoring.

Accordingly, the continuous blood pressure measurement device is capable of obtaining arterial blood pressure measurements with high accuracy by utilizing a volume compensation method in conjunction with a control unit and an extraction unit.

BRIEF DESCRIPTION OF THE DRAWINGS

FIG. 3 illustrates the operational principle of the invention.

FIG. 4 contains diagrams describing the operation of the volume servo in the control unit.

FIG. 12 presents blood pressure measurement results from two surgical patients using the Device with the MPC method, where

DETAILED DESCRIPTION

Figure 1:
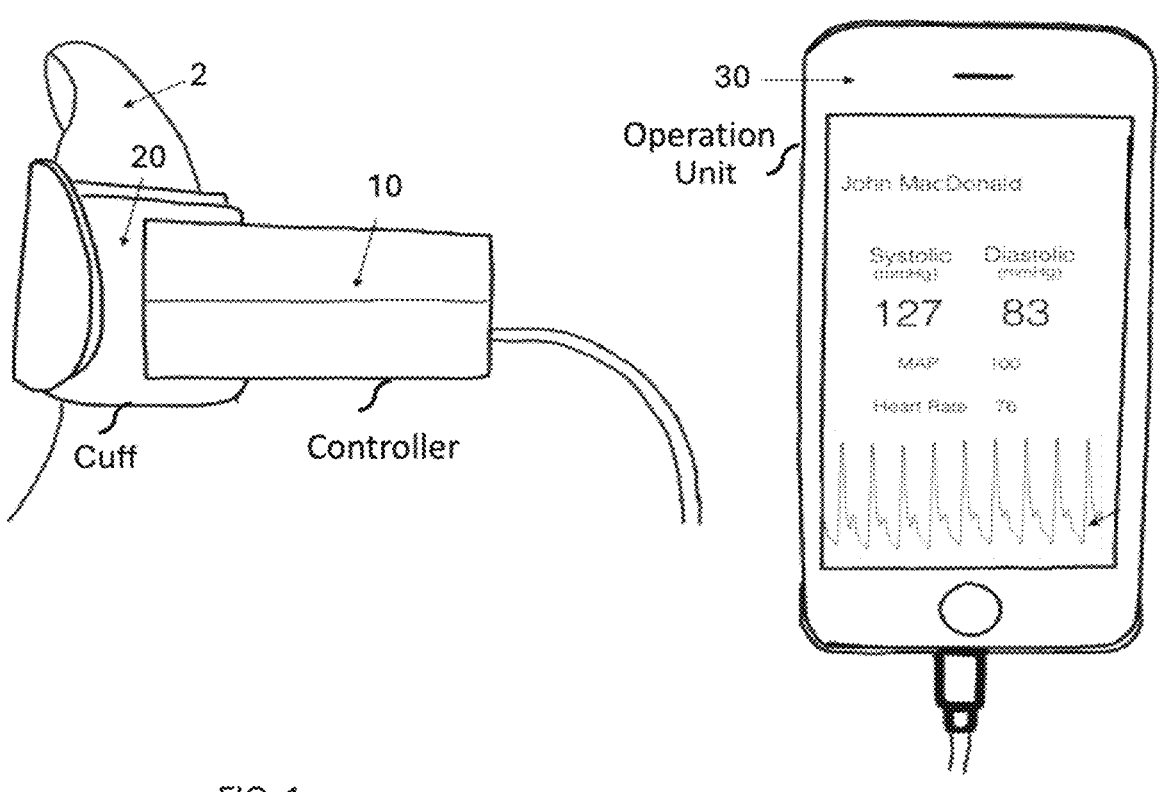
FIG. 1 is an external perspective view of a continuous blood pressure measurement device.

FIG. 1 is an external perspective view of the Device, according to one or more embodiments of the present invention. Referring to FIG. 1, the Device includes a controller 10, a cuff 20, and an operation unit 30. The cuff 20 is configured to be wrapped around a measurement site 2 of a subject. The controller 10 is attached to the cuff 20. The operation unit 30 is configured to receive user instructions and display measurements, including a blood pressure waveform, systolic pressure, diastolic pressure, mean arterial pressure, and heart rate of the subject.

In the present embodiment, the term "measurement site of a subject" refers to body parts of a subject where the cuff 20 may be applied, including, but not limited to, a finger, a wrist, and an ankle. In the following description, cuff 20 is fitted on the thumb of the subject.

Note that while a configuration in which the Controller 10 of the Device 1 in the present embodiment is attached to the cuff 20, as shown in FIG. 1, is described as an example, an embodiment is possible in which the Controller 10 and the cuff 20 are connected by an air tube (air tube 56 in FIG. 2 mentioned below), such as employed with a wrist mount monitor. Also, the Controller 10 and the operation unit 30 can be combined into one unit as an alternative embodiment.

Figure 2:
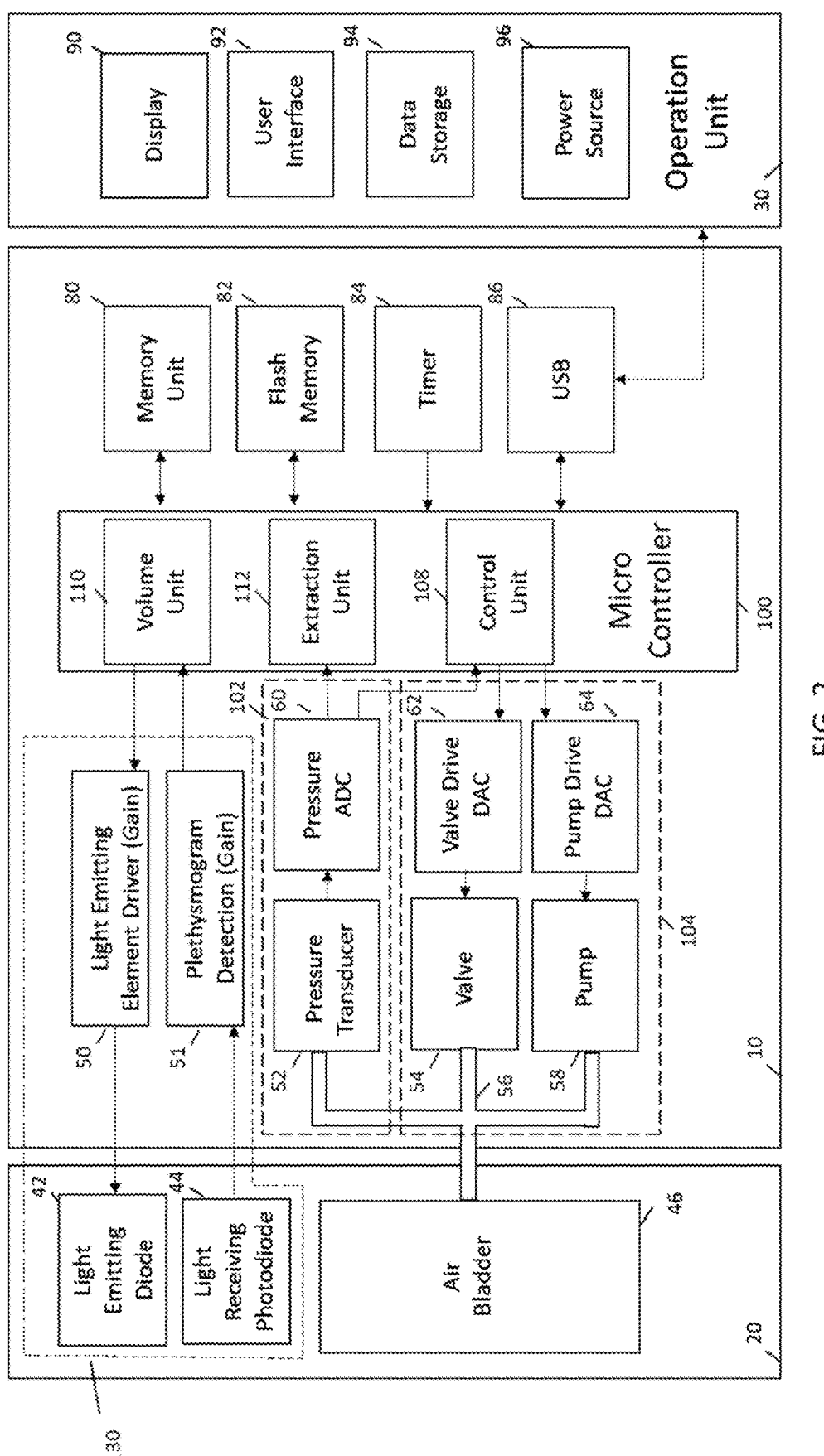
FIG. 2 is a block diagram showing the hardware configuration of the device.

FIG. 2 is a block diagram illustrating the hardware configuration of the Device, according to one or more embodiments of the present invention. Referring to FIG. 2, the cuff 20 of the Device includes an airbag 46 and a photoplethysmogram (PPG) sensor module 130, which consists of a light-emitting diode (LED) 42 and a light-receiving photodiode (PD) 44. The LED 42 emits light toward an artery, and the PD 44 receives the light that has been transmitted through or reflected by the artery. The LED 42 and PD 44 are tuned for optimal sensitivity to a wavelength of 850 nm, corresponding to the hemoglobin absorption band of red blood cells circulating through the blood vessels. It should be noted that multiple LEDs 42 and PDs 44 may be included, and the number of each component may be unequal.

Referring to FIG. 2, the light-emitting diode driving circuit 50 regulates the light emission intensity of the LED 42. The PPG detection gain circuit 51, or analog-to-digital converter (ADC) 51, amplifies the signal detected by the PD 44 from transmitted or reflected light. In one preferred embodiment, the light-emitting diode driver 50 and the PPG detection circuit 51 are integrated into a single analog front-end (AFE) circuit. In other embodiments, these components may be implemented as separate circuits.

Referring to FIG. 2, the controller 10 includes a cuff pressure detection unit 102, which comprises a pressure transducer and its corresponding ADC. The inflation/deflation system 104 includes a pump 58 and a valve 54, along with their respective driver circuits. The pump 58 supplies air to the airbag 46 via an air tube 56 to increase cuff pressure, while the valve 54 is opened or closed to release or retain air within the airbag 46 via air tube 56. The pump driver circuit 64 regulates the operation of the pump 58, and the valve driver circuit 62 controls the opening and closing of the valve 54, where both the pump driver circuit 64 and the valve driver circuit 62 may use digital-to-analog converters (DACs) circuitry to control the air pressure in the cuff collaboratively.

Referring to FIG. 2, the controller 10 comprises a microcontroller unit (MC) 100, which performs centralized control of various components and executes arithmetic processing. The MC 100 further includes computational units, such as the volume unit 110, extraction unit 112, and control unit 108, which are responsible for data acquisition and interfacing with peripheral circuitry. The volume unit 110 adjusts the gain settings for the LED driver circuit 50 and the PD driver circuit 51. The control unit 108 coordinates the operation of the pump driver circuit 64 and the valve driver circuit 62 to achieve the desired pressure in the airbag 46. The extraction unit 112 provides real-time blood pressure parameters.

Referring to FIG. 2, the controller 10 further includes a memory unit 80 for storing programs that direct the MC 100 to execute prescribed operations and manage various data. A non-volatile memory, such as flash memory 82, is used to store the bootloader and measured blood pressure data. A timer 84 tracks the current time and outputs time data to the MC 100. Additionally, a USB connection 86 links the controller 10 to the operation unit 30, enabling reception of user commands, data transmission, and power supply.

Referring to FIG. 2, the operation unit 30 includes a display unit 90 for presenting monitoring results, a user interface unit 92 for receiving user commands to power the controller 10 of the Device on or off, a data storage unit 94 for storing monitoring data, and a power source 96 for supplying power to the Device.

Figure 3A:
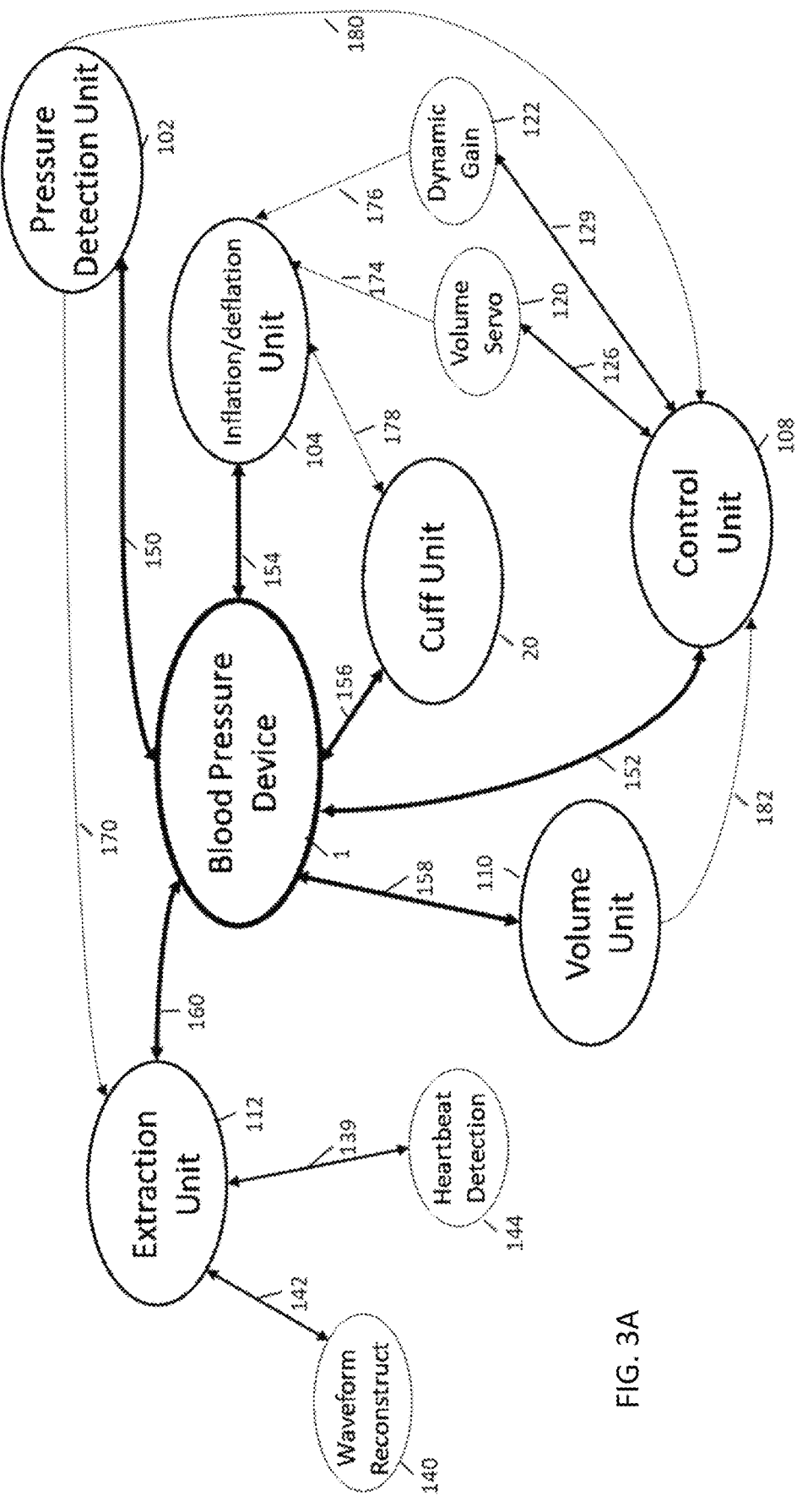
FIG. 3A is a block diagram showing functional operation.

FIG. 3A is a block diagram illustrating the functional operation of the continuous blood pressure measurement device 1, according to one or more embodiments of the present invention. As shown in FIG. 3A, the Device 1 may include a finger cuff unit 20 wrapping around to a subject's measurement site 2 that maybe finger, wrist, arm, or ankle, an inflation/deflation unit 104 that supplies proper air pressure to the cuff airbag 46, a pressure detection unit 102 that measures the air pressure inside the cuff airbag 46, a control unit that commands the inflation/deflation unit 104 to generate a desired pressure value inside the cuff airbag 46, a volume unit 110 that measures the artery volume at the subject's measurement site 2, and an extraction unit 112, which reconstruct the artery pressure waveform and generates the system outputs. Bold double arrows 150, 152, 154, 156, 158, and 160 connect the blood pressure device 1 to its component units.

Referring to FIG. 3A, the control unit further includes a volume servo module 120 that is the key to the operation of the continuous blood pressure measurement device 1, and a dynamic gain adjustment module 122 that prevents the volume servo 120 from vibration and ensures it operate at an optimum condition. Double arrows 126 and 129 connect the control unit 108 to its component modules.

Referring to FIG. 3A, the volume unit converts the PPG from the PPG sensor module 130 into the volume of a blood vessel per unit length and adjusts photodiode circuitry to enhance the signal to achieve an optimal signal to noise ratio.

Referring to FIG. 3A, the extraction unit further includes a heartbeat detection module 144 that extracts systolic, diastolic, and mean arterial pressures, as well as the heart rate of every heartbeat, a waveform reconstruction module 140 that reconstruct the true pressure waveform when the volume set point is under the mean arterial pressure. Double arrows 142 and 139 connect the extraction unit 112 to its component modules. It should be noted that the heartbeat detection module 144 not only reports the blood pressures for patient monitoring display but also services the control unit to regulate timing for the control unit 108, which must coordinate the different subunits such as the model-based predictive control and proportional-integral-derivative control. Therefore, it not only reports the systolic and diastolic pressures, but also the times when they occur in real-time. Therefore, it is unique and innovative.

Referring to FIG. 3A, the operations of the continuous blood pressure measurement device 1 are described in more detail. The pressure detection unit 102 and the volume unit 110 are constantly sensing the blood measurement site 2. Using the signals from the pressure detection unit 102 and the artery volume in the volume unit 110, the control unit 108 invokes the volume servo 120 to command the inflation/deflation unit 102 respectively. At each sampling point, the dynamic gain adjustment module detects if vibration occurs, if so the global gain of the controller 108 is decreased. It also checks the volume error, if it exceeds a threshold, the global gain of the controller 108 is increased. The heartbeat detection module 144 in the extraction unit 112 takes the cuff pressure from the pressure detection unit 102, to detect heartbeat using the pressure waveform. It generates the systolic, diastolic, and mean arterial pressures, as well as the heart rate as the outputs. The display unit 90 displays these parameters with the pressure waveform as the system output. In the case the setpoint is below the mean arterial pressure for patient comfort, the waveform reconstruction unit 142 will reconstruct the true pressure waveform before the beat detection. Here arrows 170, 174, 176, 178, 180, and 182 indicate the signal links.

Figure 3B:
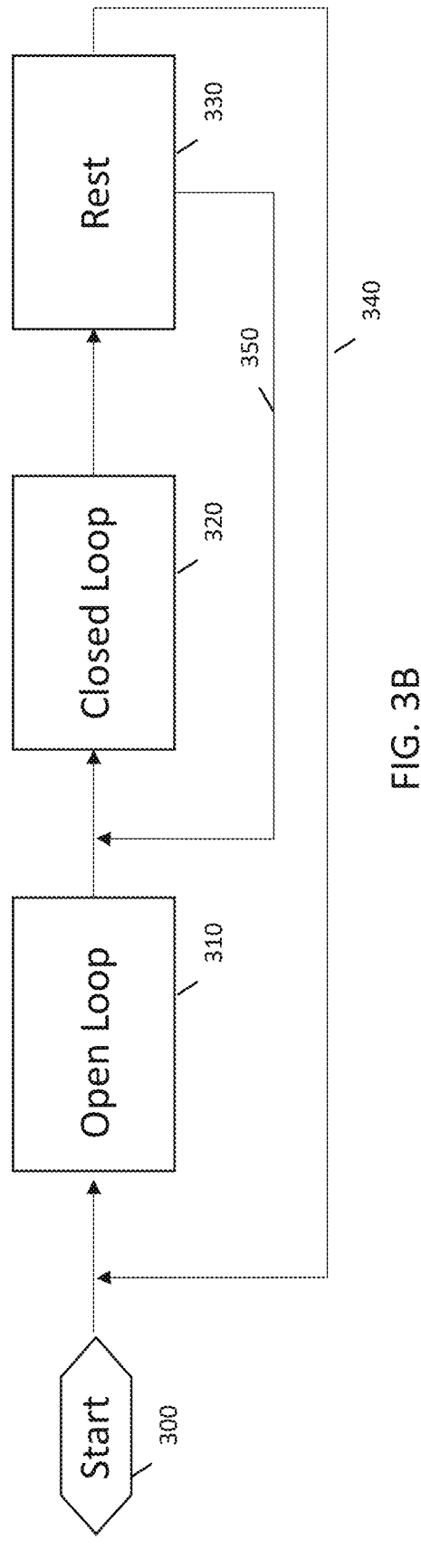
FIG. 3B is a flowchart of the device's operation sequence.
Figure 5:
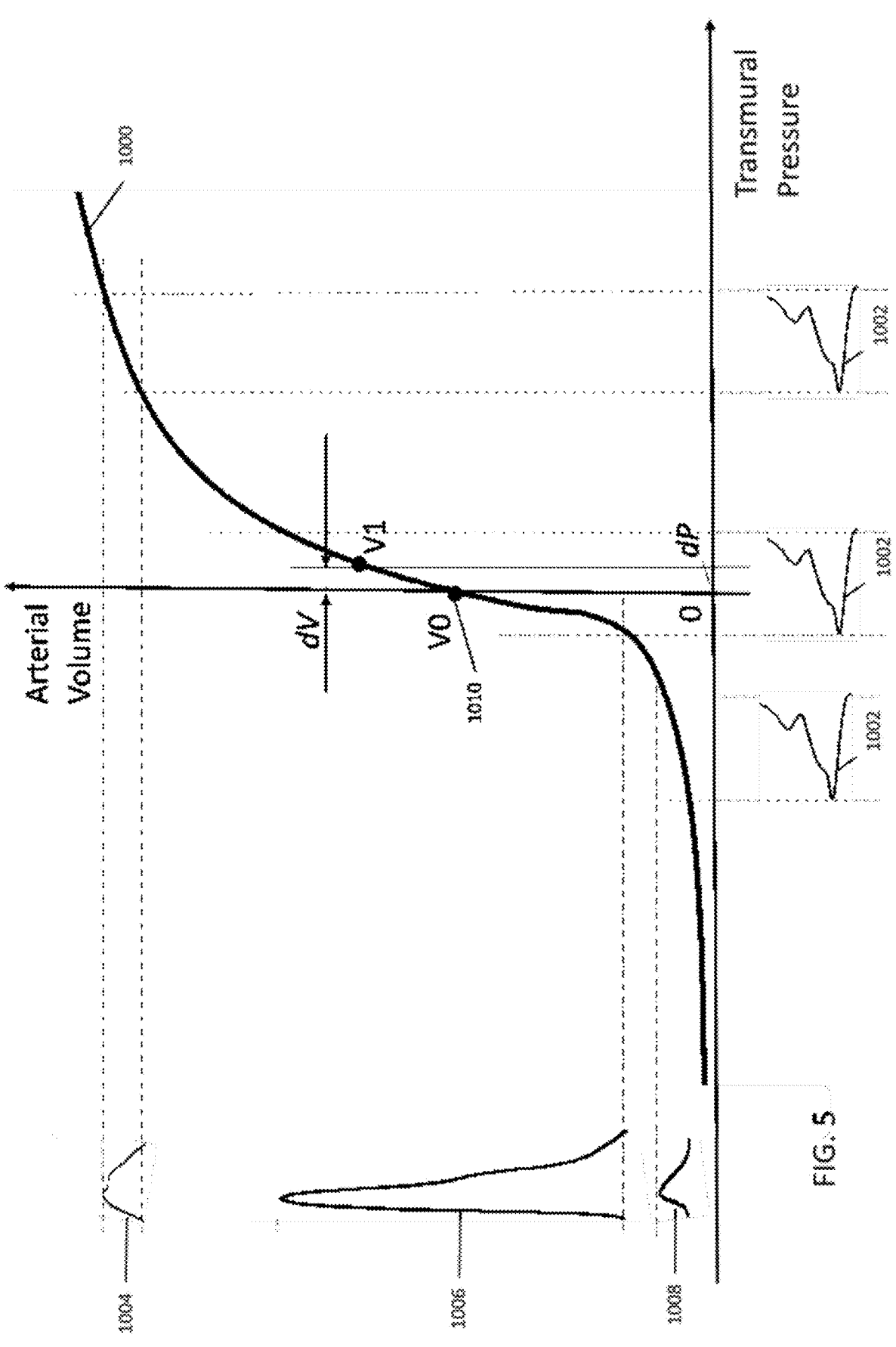
FIG. 5 is a graph showing the use of arterial mechanical properties as the artery model in the control unit.

FIG. 3B is a flow chart illustrating the operation sequence of the continuous blood pressure measurement device 1 using the volume compensation method, according to one or more embodiments of the present invention. Referring to FIG. 3B, the blood pressure measurement starts at 300, where the power is on and the continuous blood pressure measurement device 1 is properly initialized. During the open-loop operation 310, the artery mechanical property of the subject shown in FIG. 5 is characterized and stored in the memory unit 80. Then the closed-loop 320 is in operation, which includes the control unit and extraction, to deliver the artery pressure waveform and the parameters including the systolic, diastolic, mean arterial pressures, and the heart rate. After that an appropriate rest period is programmed, to allow the measurement site rest, to improve the comfort of the subject. Then the system can continue the closed-loop monitoring, or back to the open-loop characterization, depending on the length of the rest time.

Figure 4A:
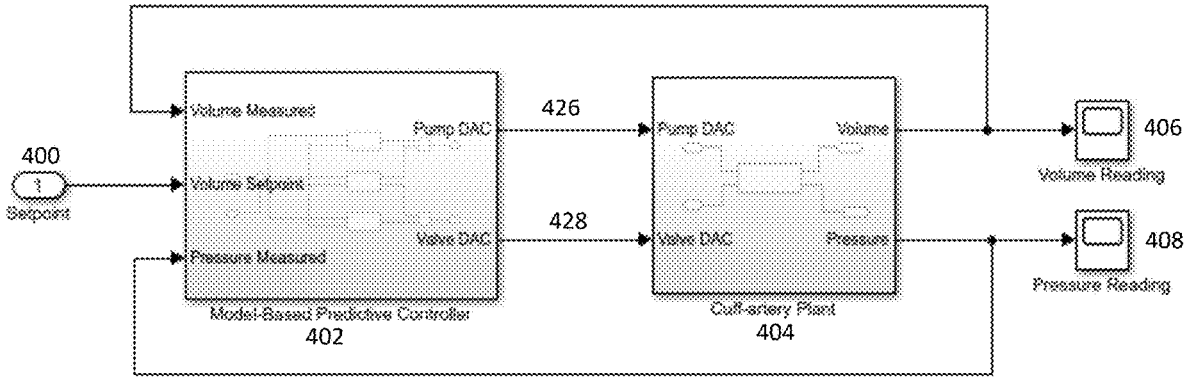
FIG. 4A shows an overview of the volume servo.

FIG. 4 includes two diagrams illustrating the volume servo 120 in control unit 108, which regulates inflation and deflation of the cuff airbag 46, according to one or more embodiments of the present invention. FIG. 4A provides an overview of the volume servo. System inputs include the volume setpoint 400, along with pressure and volume measurements from sensors 406 and 408, respectively. A model-based predictive controller (MPC) 402 calculates and sets the pump and valve DACs as outputs to their respective circuits. The cuff-artery plant 404 represents the physical response of the test subject. The sensed volume and pressure are fed back to the MPC via sensors 406 and 408. Notably, DACs may be substituted with Pulse Width Modulation (PWM) if an alternative driver design is used for the pump and valve. Such a change does not affect the validity of subsequent sections, provided PWM is used in place of DAC.

Referring again to FIG. 4, FIG. 4B illustrates the internal structure of the MPC 402. The system receives three inputs: volume setpoint 400, measured volume from sensor 406, and measured pressure from sensor 408. The measured pressure 408 is directed to the pump controller 416, valve controller 420, and system model 418. Simultaneously, the volume setpoint 400 is compared with the measured volume 406 at adder 412, producing an error signal 413. This error is scaled by a global gain 410 and then fed into controllers 416 and 420.

Figure 4B:
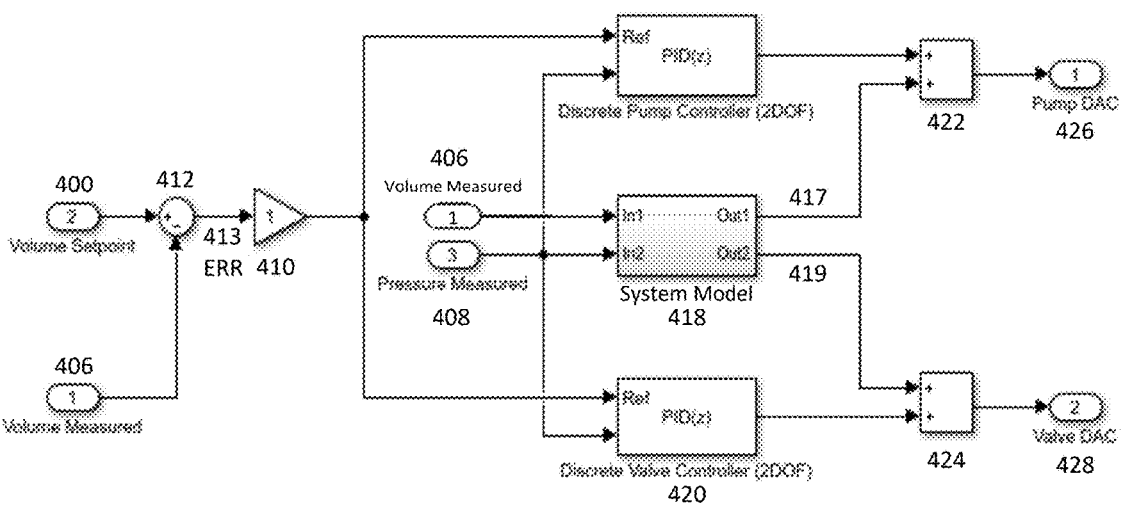
FIG. 4B shows details of a model-based predictive controller (MPC).

Referring to FIG. 4B, the pump and valve controllers 416 and 420 are discrete-time proportional-integral-derivative (PID) controllers with two-degrees-of-freedom (2DOF), as represented by the following equation:

$$P(br - y) + I \cdot T_s \frac{1}{z-1}(r-y) + D \frac{N}{1+N \cdot T_s \frac{1}{z-1}}(cr-y) \qquad \text{(Eq. 1)}$$

Where r is the volume setpoint, y the measured volume, P, I, and D is the proportional, integral, and derivative coefficients, $T_s$ is the sampling time, and N is the filter coefficient for the derivative, and b and c are the weights for the setpoint. With advanced features such as setpoint weighting, anti-windup, external reset, and signal tracking, the controller can be tuned accurately for the target plant 404.

Figure 6:
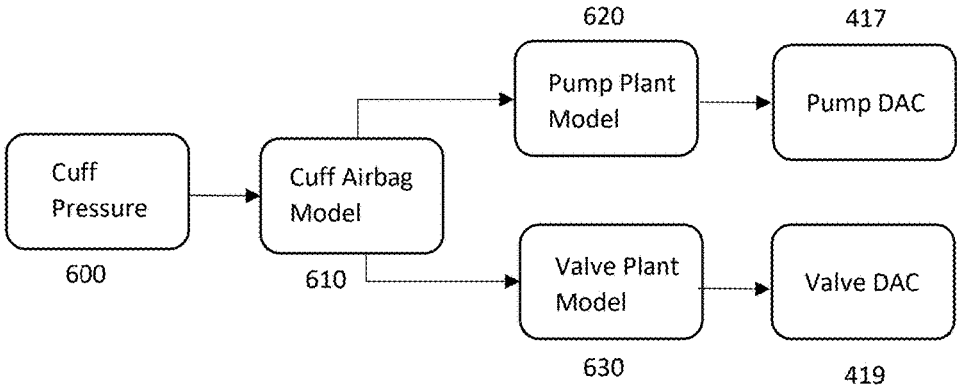
FIG. 6 illustrates a cuff plant model that consists of a pump, a valve, and an airbag.
Figure 7:
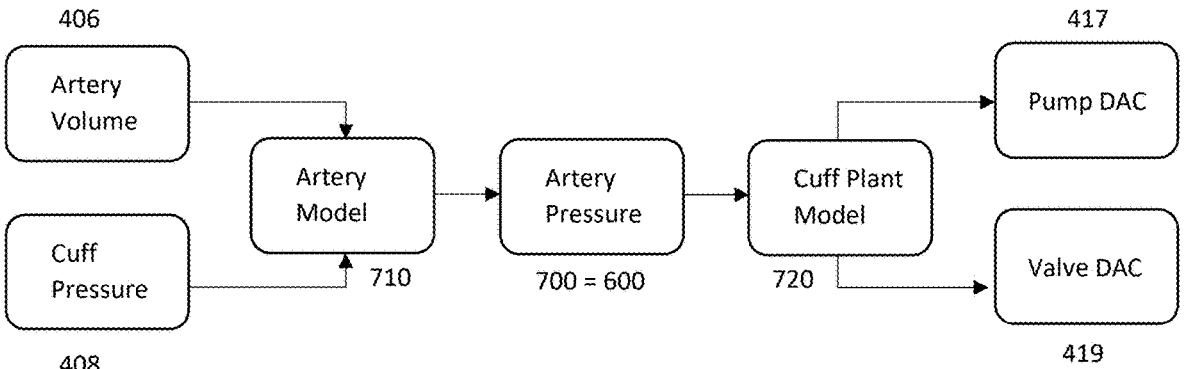
FIG. 7 illustrates a system model structure for the MPC.

Referring to FIG. 4B, a System Model is employed, which described in detail in FIG. 7. The comprises an artery mechanical model and a cuff plant model, which will be explained further in FIG. 5 and FIG. 6, respectively. At runtime, the cuff plant model generates desired pump and valve DAC values 417 and 419, which are combined with the outputs of PID controllers 416 and 420 via adders 422 and 424, respectively, producing the final pump DAC 426 and valve DAC 428. It should be noted that the DACs from 417 and 419 can be weighted, thus the adders 422 and 424 can be weighted addition, with actual weighting function be performed in either the system model or the 2DOF PID controller. The design and implementation of 2DOF PID controllers for common payloads is a well-established practice. Tools like MATLAB and Simulink offer robust frameworks for designing and simulating 2DOF PID controllers, as detailed in their documentation (https://www.mathworks-.com/help/slcontrol/ug/designing-two-degree-of-freedom-pid-controllers.html). Further guidance is available in academic and industrial literature, such as *A Guide to Design MIMO Controllers for Architectures* by Raghavendra Pradyumna Pothukuchi and Josep Torrellas, University of Illinois at Urbana-Champaign (http://iacoma.cs.uiuc.edu).

The novelty of the present invention lies in the integration of model-based predictive control (MPC) with a two-degree-of-freedom (2DOF) PID controller. The MPC accounts for complex nonlinearities and time delays inherent in biological and electromechanical systems, while the 2DOF PID controller provides rapid response to time-varying disturbances. This combined approach enables precise setpoint tracking, even as the mechanical properties of the artery and surrounding tissue evolve over time.

In a preferred embodiment, the pump is a piezoelectric type that permits backward leakage of pneumatic pressure. Accordingly, the control strategy aims to minimize pump power consumption by setting the valve to a minimal leakage state within model 418. In an alternative embodiment, the valve may be replaced with a fixed orifice. In this configuration, components 420, 424, and 428 are unnecessary, and the pump alone regulates the cuff airbag 46.

FIG. 5 illustrates the use of arterial mechanical properties as the artery model, according to one or more embodiments of the present invention. Curve 1000 shows the relationship between transmural pressure (horizontal axis) and arterial volume VV (vertical axis), where transmural pressure is defined as arterial pressure minus cuff pressure. The curve exhibits significant nonlinearity. Waveform 1002 represents an arterial pressure waveform applied at three different points along the curve. When transmural pressure equals zero—indicating the equilibrium state V0, where the arterial wall is unloaded—arterial compliance (i.e., the change in volume due to pulsatility) is at its maximum, as shown by 1006. When transmural pressure deviates from zero, compliance decreases, and the shape of the volume waveform changes, as shown in 1004 and 1008. The point where transmural pressure is zero is critical, as it allows arterial pressure to be directly inferred from cuff pressure. Identifying this zero point is central to accurate blood pressure measurement.

During the operation of the volume servo 120, the artery volume is controlled at the set point V0 1010, at which the artery is at an unloaded state. By measuring dV at V1 as the signal line 413 in FIG. 4, the controller change dP can be obtained using the following equation:

$$dP = F(dV) \qquad \text{(Eq. 2)}$$

Here the function F represents the mechanical property curve of an artery 1000, which can be implemented as a close form function, or a discrete lookup table, or a combination of both, by these skilled at the art. Further from the fact that at the unloaded point V0, $$Pa=Pc \tag{Eq. 3}$$

Where Pa is there arterial pressure, and Pc is the cuff pressure. Then it can be derived that $$Pa'=Pc+dP \tag{Eq. 4}$$

FIG. 6 illustrates the cuff plant model, according to one or more embodiments of the present invention. Referring to FIG. 6, the cuff plant model comprises a cuff airbag model 610, a pump plant model 620, and a valve plant model 630. The cuff airbag model 610 includes the volume of the airbag, the materials used, and the air tube 56 in FIG. 2, which completely characterize the mechanical properties of airbag related to the cuff pressure. It should be noted that the airbag model 610 can be either described explicitly in mathematical formula, or implicated by using as the payload when deriving the pump and valve plant models. The pump and valve plant models reflect the electromechanical characteristics of the system's pump and valve and can be developed using standard system identification methods known to those skilled in the field. Modeling the electromechanical behavior of the pump and valve is a well-established practice, with extensive implementation resources available. Tools like MATLAB and Simulink offer robust system identification frameworks, as detailed in the System Identification Toolbox documentation (https://www.mathworks.com/products/sysid.html). Manufacturers also typically provide pressure and flow versus voltage curves, which serve as useful references during modeling. Voltage values can be converted to DAC units using the digital-to-analog converter specifications provided by the manufacturer. The general form of the cuff plant model is expressed as:

$$G_i=f(Pc_i,G_{i-1}), \text{ and } G=\{DACp,DACv\}. \tag{Eq. 5}$$

Where Pc is the cuff pressure, DACp, DACv are the DAC values for the pump and valve, respectively. While Eq. 5 is a conceptual representation of the cuff plant model. This equation is meant to express the idea that G, including both DACp for the pump and DACv for the valve, are updated simultaneously and collaboratively for better performance for each control step, as one of the advantages of the present invention. It should also be noted that the relationship $f$ can be either an explicit mathematical function like a transfer function and linear regression, or as a table, a neural network, or other forms of implicit relationships used in programming of a control system.

FIG. 7 illustrates the System Model 418, according to one or more embodiments of the present invention. The System Model 418 comprises the artery model 710 and the Cuff Plant Model 720 consecutively. Using the artery volume 406 and cuff pressure 408 as input, the artery model 710 produces the arterial pressure 700, as illustrated in FIG. 5. Since the goal of control unit is to make the cuff pressure 600 track the arterial pressure 700, they can be treated as equal. Then using the cuff plant model as described in FIG. 6, the pump and valve DACs 417 and 419 can be obtained.

Figure 8:
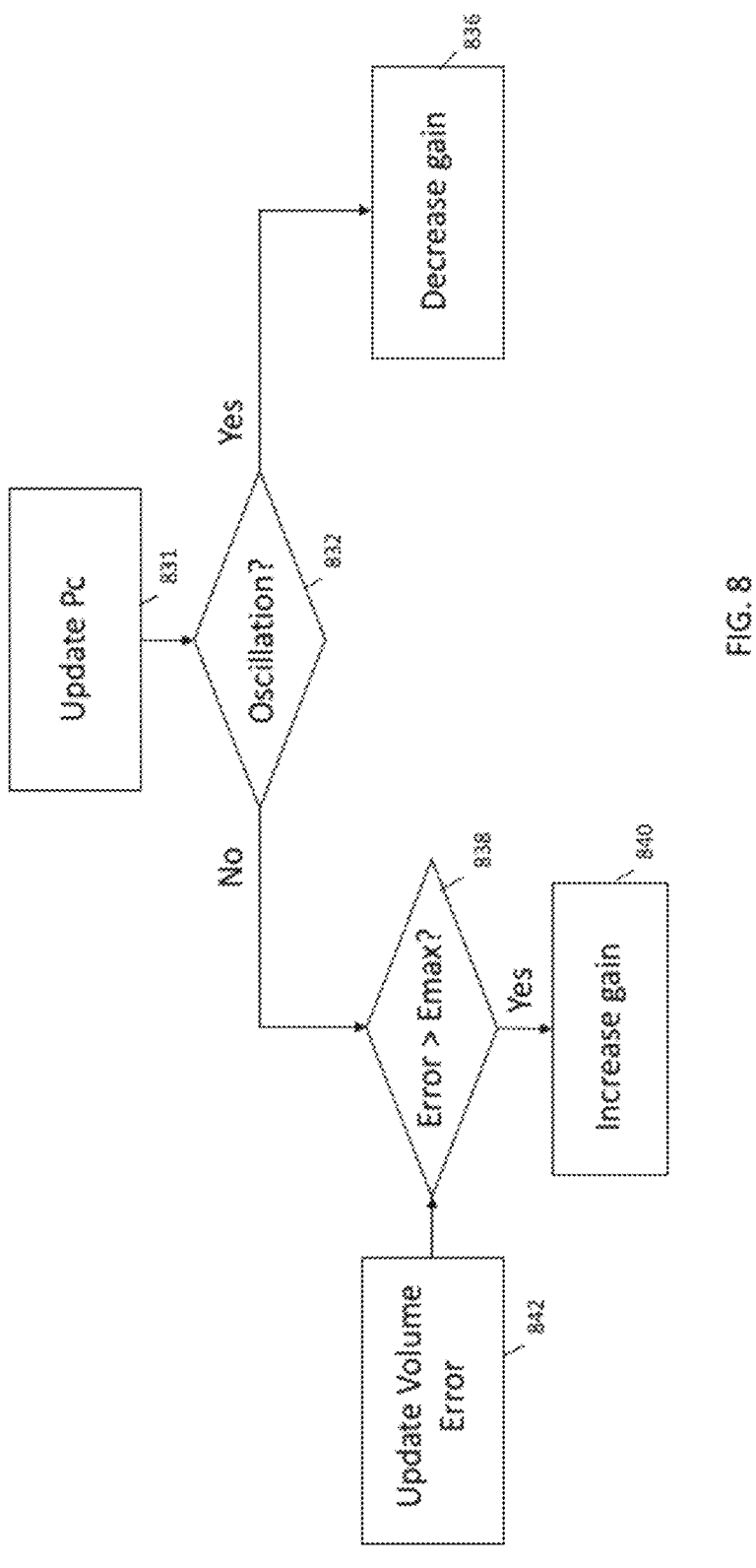
FIG. 8 is a flowchart describing the global gain adjustment for the control unit.

FIG. 8 is a flowchart describing the global gain 410 adjustments for the model-based predictive controller 402 in the control unit 108, according to one or more embodiments of the present invention. Referring to FIG. 8, the input to the module is the cuff pressure Pc and it is updated in step 831. The system vibration is checked at step 832, which is well known to the person skilled in the art. The widely used methods include Eigensystem Realization Algorithm (ERA), Micro-Electro-Mechanical Systems (MEMS)-Based Vibration Monitoring, and Bayesian Operational Modal Analysis (BAYOMA). If a vibration is detected, global gain 410 is decreased in step 836 and resumed to the controller operation of the MPC 402. If a vibration is not detected, then the volume error is updated at step 842 and the magnitude of the error is checked against the Emax at step 638, which will be further explained in FIG. 8. If the condition is met, then global gain 410 is increased at step 840.

Figures 9, 9A, 9B, 9C:
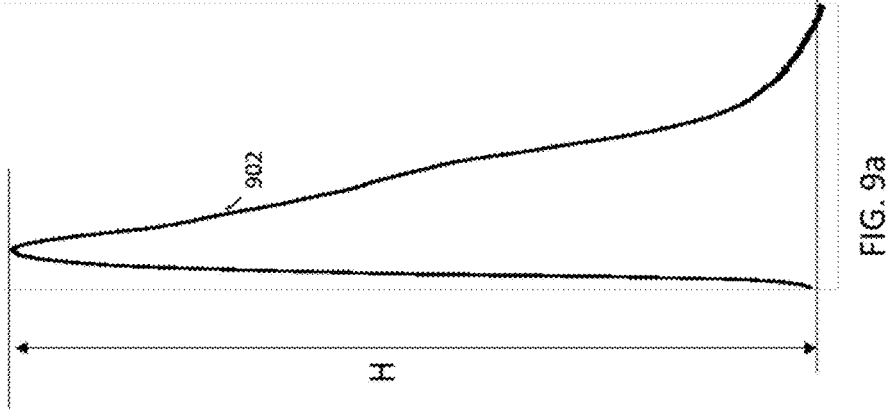
FIG. 9 illustrates the error correction method in the extraction unit.
FIG. 9a shows a single-heartbeat volume waveform from open-loop characterization.
FIG. 9b shows multiple-heartbeat waveforms during volume clamping.
FIG. 9c illustrates the bilinear transformation process for correction.

FIG. 9 is a diagram illustrating the error correction method in the extraction unit 112, according to one or more embodiments of the present invention. Referring to FIG. 9, FIG. 9*a* further illustrates a volume waveform 902 that contains one heartbeat and is obtained during the open-loop characterization. The height H indicates the maximum change in volume due to the artery pulsation. FIG. 9*b* further illustrates a volume waveform 904 that contains several heartbeats and is obtained during the closed-loop for volume clamp. Using the control unit described in the above sections, high accuracy is achieved, which results in small height h, indicating a small control error during the blood pressure measurement phase. However, the volume errors in FIG. 9*b* suggest that further correction can be used to further increase the accuracy of the pressure waveform. FIG. 9*c* shows the process of a bilinear transformation for the correction.

Denote x for the artery volume, y for the cuff pressure, and f for the artery pressure. In bilinear interpolation, the interpolating function is of the form $$f(x,y)=a_{xy}xy+b_xx+b_yy+c \tag{Eq. 6}$$

For the 4 points shown in FIG. 9*c*, there are 4 vertexes that can be obtained from the mechanical property curve 1000 in FIG. 5 that is corresponding to the peak values of points 1 and 2, and valley points 3 and 4. Then $$f(x_1,y_1)=a_{xy}x_1y_1+b_xx_1+b_yy_1+c=f1$$

$$f(x_2,y_2)=a_{xy}x_2y_2+b_xx_2+b_yy_2+c=f2$$

$$f(x_3,y_3)=a_{xy}x_3y_3+b_xx_3+b_yy_3+c=f3$$

$$f(x_4,y_4)=a_{xy}x_4y_4+b_xx_4+b_yy_4+c=f4 \tag{Eqs. 7}$$

Let $\mu=\{a_{xy} \; b_x \; b_y \; c\}$, F=$\{f1 \; f2 \; f3 \; f4\}$, and $$X = \begin{vmatrix} x1y1 & x1 & y1 & c \\ x2y2 & x2 & y2 & c \\ x3y3 & x3 & y3 & c \\ x4y4 & x4 & y4 & c \end{vmatrix} \tag{Eq. 8}$$

then the bilinear equation coefficient vector u can be solved for the linear system equation as $$X\mu=F, \tag{Eq. 9}$$

where X is the coefficient matrix in the above equation. With $\mu$ now $f(x,y)$, that is the arterial pressure, can be obtained using Eq.6.

This bilinear transform can be extended to improve the patient's comfort while reconstructing the measured arterial pressure, as described in the following section.

Figure 10:
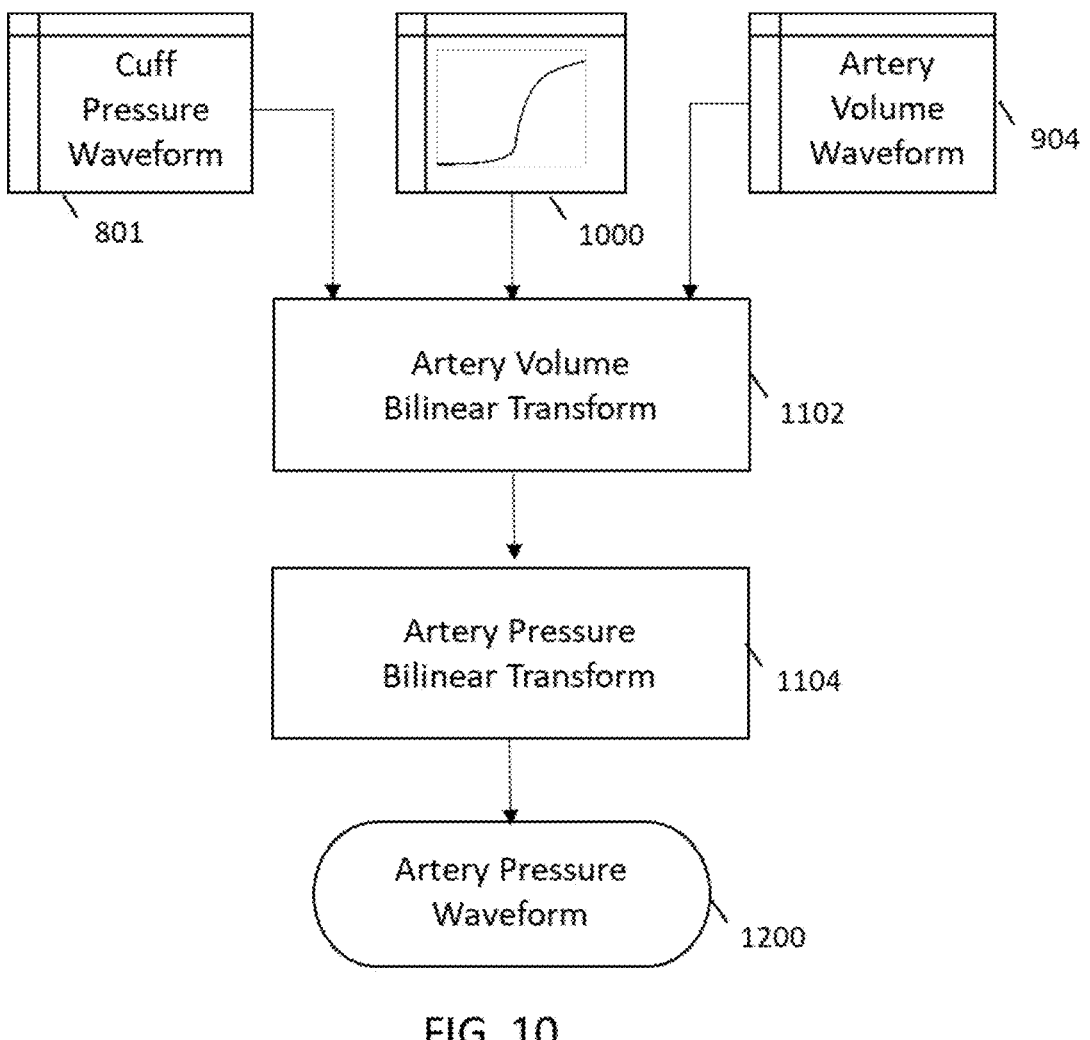
FIG. 10 is a flowchart illustrating the arterial pressure reconstruction method in the extraction unit.

FIG. 10 is a flow chart illustrating the arterial pressure reconstruction method in the extraction unit 112, according to one or more embodiments of the present invention. Referring to FIG. 10, the reconstruction takes the cuff pressure waveform 801 and arterial volume waveform 904 as the input and utilizes the artery mechanical property 100 as the base function. Since the setpoint is purposely set to a lower value than the one corresponding to the mean arterial pressure value, the cuff pressure waveform 801 shown in FIG. 1l is lower than the true arterial waveform, also the pulse pressure is smaller. The first step is to reconstruct the true volume waveform. This is because when the setpoint is lower, the volume magnitude is smaller, as shown in FIG. 5 Volume 1004 compared to the true volume 1106. The bilinear transformation can be done using Eq. 6-9 but replace f with V for volume. Once the true volume waveform is obtained, the Eq. 6-9 can be used as described above to reconstruct the arterial pressure Pa.

Figure 11:
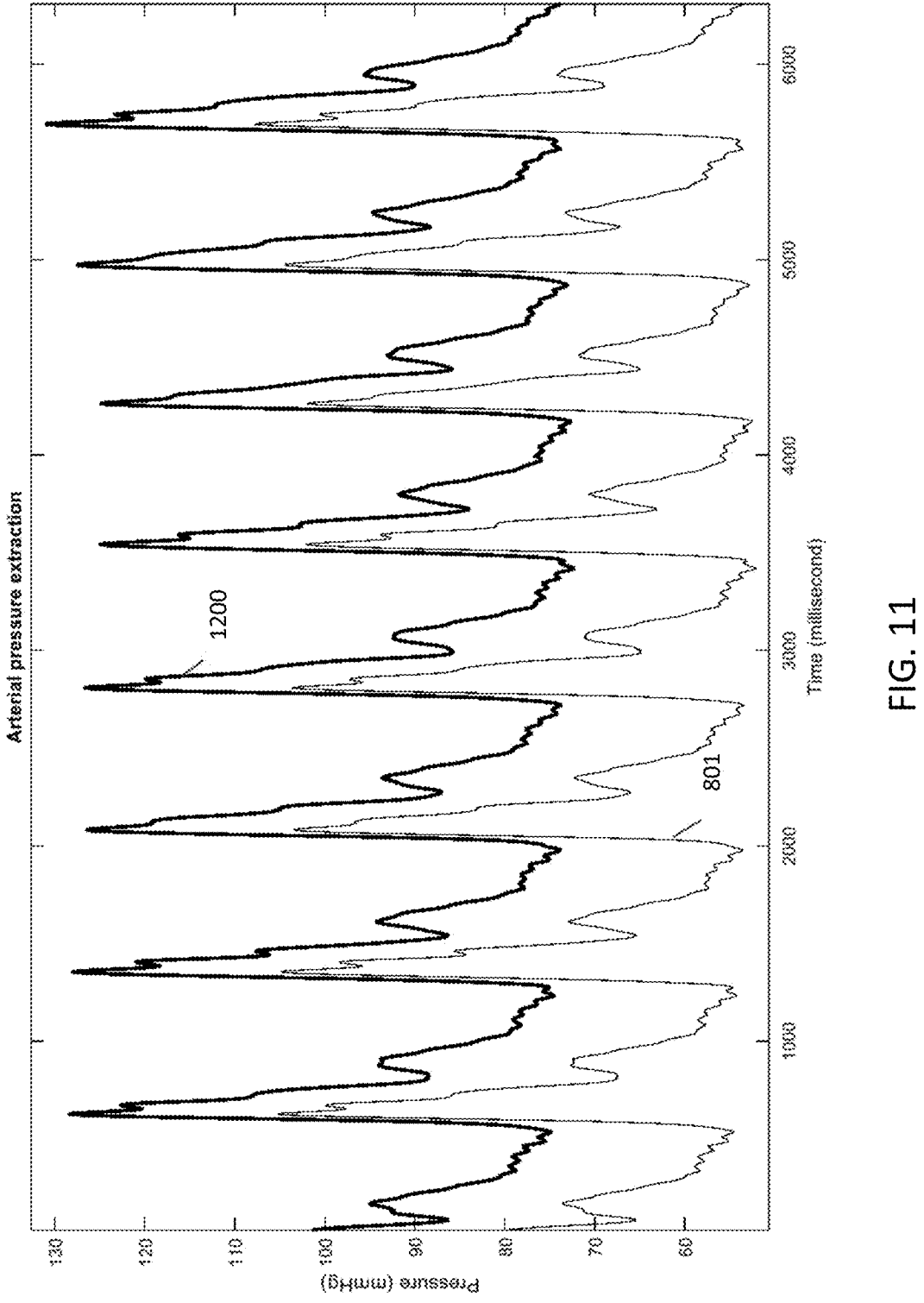
FIG. 11 is a waveform chart showing the result of arterial pressure waveform reconstruction.

FIG. 11 is a waveform chart showing the arterial pressure waveform reconstruction result, according to one or more embodiments of the present invention. Referring to FIG. 11, the waveform 801 is the cuff pressure, and the waveform 1200 is the reconstructed arterial pressure, which accurately measures the blood pressure.

FIG. 12 presents the comparative test results from two adult surgical patients using the Device in a hospital-based configuration and operating in continuous mode. Both patients required radial intra-arterial catheter (A-line) invasive blood pressure (IBP) monitoring during major abdominal surgeries, which serves as the reference device. The A-line was placed in accordance with hospital protocols. Simultaneously, the Device was worn on the thumb of the same arm. Measurements were recorded under general anesthesia, beginning at the induction phase and continuing until either the A-line or the Device was no longer available. This monitoring period captured a wide range of blood pressure fluctuations. Both BP waveform data streams were recorded simultaneously. After data acquisition, the waveforms from the Device and A-line were aligned in time and directly compared.

Figures 12A, 12B:
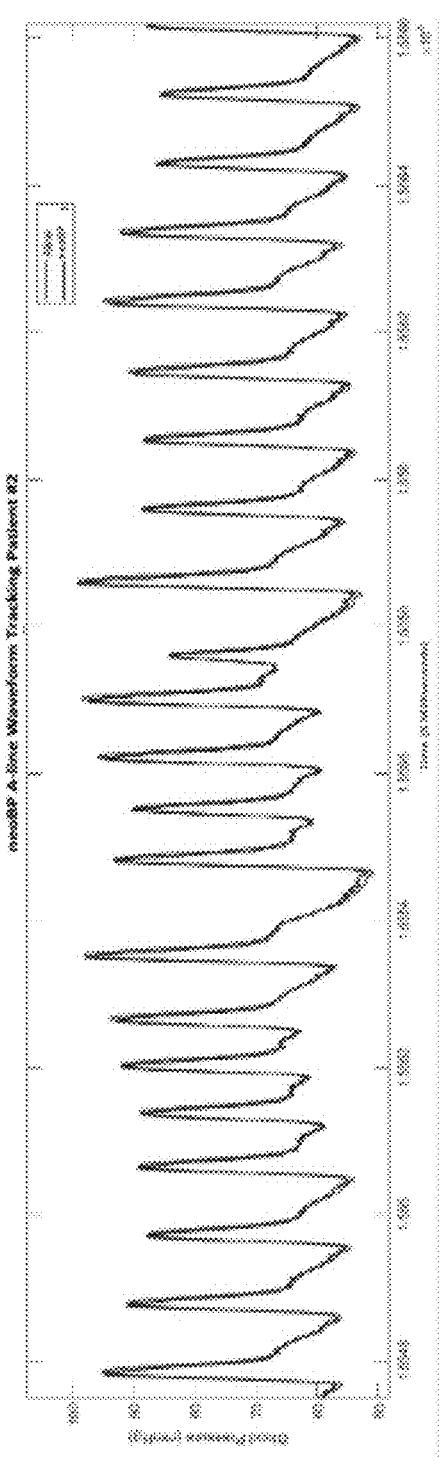
FIG. 12A depicts the waveform tracking performance.
FIG. 12B illustrates systolic and diastolic pressure tracking over time.

FIG. 12A illustrates the waveform tracking performance, showing that the waveform generated by the Device (blue) closely tracks the A-line waveform (red), even during significant blood pressure fluctuations.

FIG. 12B presents systolic and diastolic pressure tracking over time, highlighting the stability of the Device. The two signals overlap for approximately 3.1 hours, during which all detected beats were included, except for brief periods when the pressure-volume function was being constructed or updated. In this figure, the systolic and diastolic values (green and blue) from the Device closely track their arterial counterparts (red and magenta), even during significant blood pressure variations, including fluctuations exceeding 50 mmHg. These results demonstrate that the present invention meets and exceeds the stability and blood pressure change criteria for a Type A device in accordance with ISO 81060-3 industry standards.

Figures 12C, 12D:
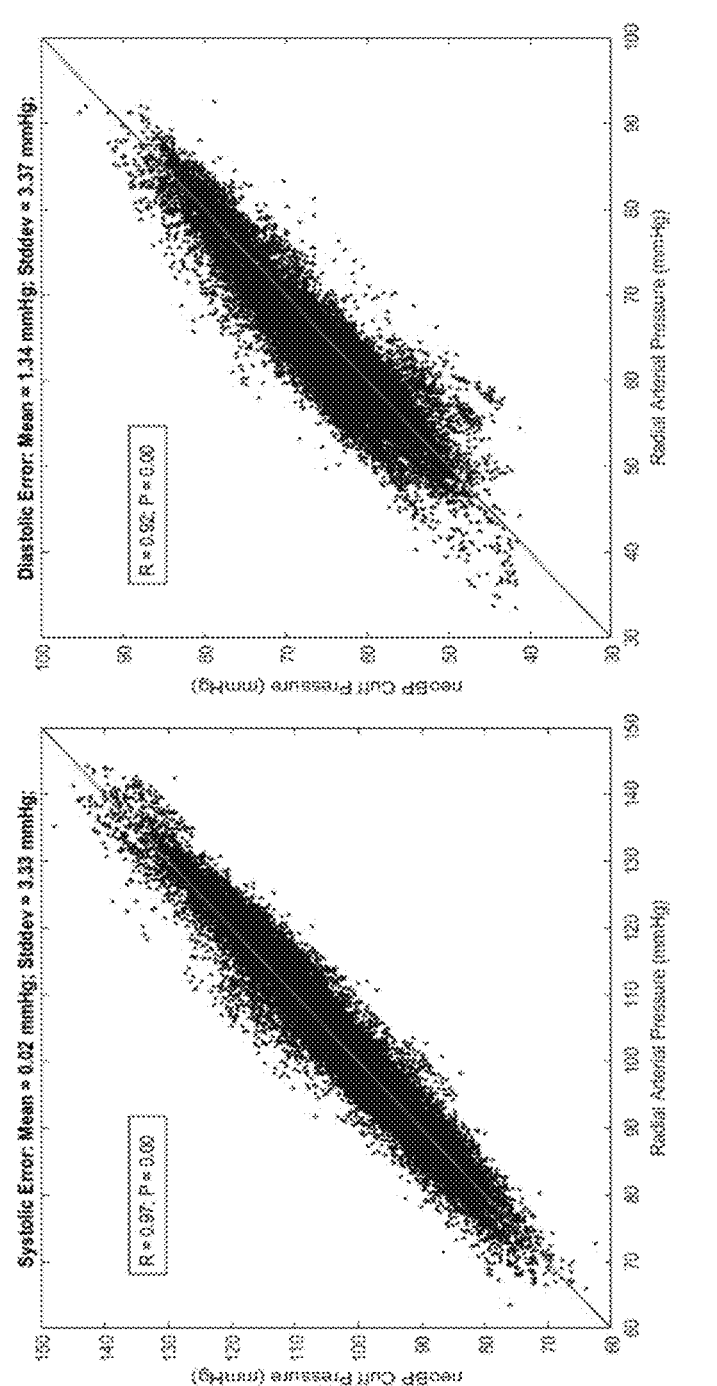
FIG. 12C presents an error scatter plot, FIG. 12D provides statistical analysis of measurement errors.

FIG. 12C presents the error scatter plot for the overall correlation comparisons from the test, which includes 24,829 data points collected over approximately 7.6 hours. The largest 0.1% of error data were excluded as statistical outliers. The correlations between the A-line and the Device for systolic and diastolic pressures were 0.97 and 0.92, respectively, demonstrating a high level of agreement between the two measurement methods.

FIG. 12D provides the error statistics, confirming that the Device achieves an accuracy of 3±5 mmHg (mean error±standard deviation), surpassing the most stringent AAMI 81060-2 standard of 5±8 mmHg. These results strongly suggest that the present invention is performing as intended within a surgical setting.

An extraction unit and a method for deriving the relationship between transmural pressure and volume (P-V function) as the system model, similar to that described in U.S. patent Ser. No. 17/517,283, is used, which is incorporated herein by reference. The novel features include linearizing the plethysmogram using a logarithmic transform, a P-V function building process comprising a starting point, a flat phase, a ramp-up phase, a stop point, and a ramp-down phase. Additionally, the extraction unit is configured to utilize a curve-fitting method to perform a breathing noise removal process, which eliminates noise introduced by the subject's breathing. The breathing noise removal process is performed using a sinusoidal function, and a setpoint is derived. This setpoint, together with the system model, is used for subsequent continuous mode operation. Finally, the extraction unit is also able to detect not only systolic and diastolic pressures, but also the precise times these pressures occur. These features collectively ensure that the Device achieves the target accuracy reliably.

The invention claimed is:

1. A continuous blood pressure measurement device for measuring arterial blood pressure, comprising:
   a cuff that is configured to fit on a blood pressure measurement site to compress an artery of the measurement site;
   an inflation/deflation unit that consists of a piezoelectric pump and a valve, to increase and decrease a pressure inside the cuff;
   a pressure detection unit that is configured to detect a cuff pressure, which is the pressure inside the cuff;
   at least one light-emitting diode and at least one photodiode, wherein at least one pair of the light-emitting diode and the photodiode is configured to generate photoplethysmogram;
   a volume detection unit that is configured to detect an arterial volume signal indicating a volume of the artery per unit length;
   a control unit that is configured to set the cuff pressure by controlling the inflation/deflation unit, wherein the control unit comprises a model-based predictive controller to output digital to analog converter (DAC) signals to both pump and valve simultaneously, wherein the model-based predictive controller comprises a system model and a two-degree-of-freedom (2DOF) proportional-integral-derivative (PID) controller, wherein the system model incorporates arterial mechanical properties and cuff plant electromechanical properties, and wherein a global gain adjustment is used to prevent system vibration and improve performance;
   and an extraction unit that is configured to measure volume and blood pressure waveforms to detect systolic with systolic timing, diastolic with diastolic timing, and mean arterial pressure (MAP) of a subject, wherein a bilinear transformation is used for error correction, wherein a volume setpoint corresponds to the cuff pressure below the mean arterial pressure to prevent skin discoloration, wherein the extraction unit is further configured to construct a true blood pressure waveform using a lower cuff pressure to improve subject comfort.

2. The continuous blood pressure measurement device of claim 1, wherein the cuff is applicable to the measurement site, wherein the measurement site includes at least one of the subjects' fingers, wrists, or ankles, where the wrists and ankles are preferred measurement sites for infants and thumbs are for other age groups.

3. The continuous blood pressure measurement device of claim 1, wherein the valve comprises at least one of a piezoelectric valve, a solenoid valve, an electromechanical valve, or a fixed orifice, which is configured to release pneumatic pressure in a cuff airbag and wherein pneumatic pressure is modulated by the pump.

4. The continuous blood pressure measurement device of claim 1, wherein the volume detection unit, the control unit, and the extraction unit operate in a CPU of a microcontroller, wherein input channels of the microcontroller comprises of digital input channels and/or analog to digital converter (ADC) input channels, and whose output channels of comprises analog output channels and/or digital to analog converter (DAC) and/or Pulse Width Modulation (PWM) output channels, hereinafter referred to as the DAC.

5. A control method of controlling a continuous blood pressure measurement device for measuring blood pressure, the method comprising:

> providing a cuff that is configured to fit on a blood pressure measurement site to compress an artery of the measurement site;
>
> increasing and decreasing a pressure inside the cuff using an inflation/deflation unit that consists of a piezoelectric pump and a valve;
>
> detecting a cuff pressure using a pressure detection unit, which is the pressure inside the cuff;
>
> generating photoplethysmogram using at least one light-emitting diode and at least one photodiode;
>
> detecting an arterial volume signal indicating a volume of the artery per unit length using a volume detection unit;
>
> setting the cuff pressure by controlling the inflation/deflation unit using a control unit, wherein a model-based predictive controller comprises a system model and a 2DOF PID controller, wherein the system model incorporates arterial mechanical properties and cuff plant electromechanical properties, wherein a global gain adjustment is used to prevent system vibration and improve performance;
>
> and measuring volume waveform and blood pressure waveform to detect systolic with systolic timing, diastolic with diastolic timing, and MAP of a subject using an extraction unit, wherein a bilinear transformation is used for error correction, wherein a volume setpoint corresponds to the cuff pressure below the mean arterial pressure to prevent skin discoloration, wherein the extraction unit is further configured to construct a true blood pressure waveform using a lower cuff pressure to improve subject comfort.

6. The control method of claim 5, wherein the system model describes nonlinear, hysteretic, and time delay system behaviors for the arterial mechanical properties and the cuff plant electromechanical properties, wherein the cuff plant properties consist of cuff airbag mechanical properties, pump electromechanical properties and valve electromechanical properties, wherein the arterial mechanical properties and the cuff plant properties are arranged sequentially and connected by an arterial pressure.

7. The system model of claim 6, wherein the arterial mechanical properties describe a relationship between the arterial volume and a transmural pressure, wherein the arterial mechanical properties outputs to the arterial pressure using the arterial volume and cuff pressure as the input.

8. The system model of claim 6, wherein the cuff plant electromechanical properties use the arterial pressure outputted from the arterial mechanical properties as the input and derives a pump DAC and a valve DAC from cuff airbag mechanical properties, pump electromechanical properties and valve electromechanical properties, wherein the cuff airbag mechanical properties can be in a form of mathematical formular or as a payload to the pump and valve, wherein the pump DAC and the valve DAC are the output of the system model for the control method.

9. The control method of claim 5, wherein the 2DOF PID controller provides the pump DAC and valve DAC to compensate the model-based predictive controllers for errors not being modeled such as the artery mechanical property changes with time, wherein the linear characterization of the 2DOF PID allows a fast control system response.

10. The control method of claim 5, wherein the inputs of the 2DOF PID controller include the volume error, the cuff pressure, and the pump and valve DAC values in the previous steps as the inputs, wherein the output of the 2DOF PID controller include the pump DAC and the valve DAC, which are generated simultaneously.

11. The control method of claim 5, wherein the pump and the valve are correlated in such a way that the valve closes as much as possible, so that an output of the pump is minimized to reduce its power usage.

12. The control method of claim 7, wherein a global gain adjustment dynamically increases the gain if a control error exceeds a threshold to improve the accuracy and decreases the gain if a system vibration is detected to eliminate the system vibration.

13. The control method of claim 5, wherein the model-based predictive controller combines the pump and valve DAC outputs from both the system model and the 2DOF PID controller to achieve optimal performance, wherein the resulting combination can be implemented as addition or weighted addition.

14. The control method of claim 5, wherein an alternative pump and valve configuration can used, such as an orifice for cuff air release, a constant output pump combined with a 3-way valve, wherein the 2DOF PID controller can be reduced to a one-degree-of-freedom (1DOF) PID controller, wherein the cuff plant can be reduced to use the valve electromechanical properties only.

15. An extraction method of measuring arterial pressures of a subject for a continuous blood pressure measurement device for measuring blood pressure, the method comprising:

> providing a cuff that is configured to fit on a blood pressure measurement site to compress an artery of the measurement site;
>
> increasing and decreasing a pressure inside the cuff using an inflation/deflation unit that consists of a piezoelectric pump and a valve;
>
> detecting a cuff pressure using a pressure detection unit, which is the pressure inside the cuff;
>
> generating photoplethysmogram using at least one light-emitting diode and at least one photodiode;
>
> detecting an arterial volume signal indicating a volume of the artery per unit length using a volume detection unit;
>
> setting the cuff pressure by controlling the inflation/deflation unit using a control unit, wherein a model-based predictive controller comprises a system model and a 2DOF PID controller, wherein the system model incorporates arterial mechanical properties and cuff plant electromechanical properties, wherein a global gain adjustment is used to prevent system vibration and improve performance;
>
> and measuring volume waveform and blood pressure waveform to detect systolic with systolic timing, diastolic with diastolic timing, and MAP of a subject using an extraction unit, wherein a bilinear transformation is used for error correction, wherein a volume setpoint corresponds to the cuff pressure below the mean arterial pressure to prevent skin discoloration, wherein the extraction unit is further configured to construct a true blood pressure waveform using a lower cuff pressure to improve subject comfort.

16. The extraction method of claim 15, wherein the bilinear transformation for error correction is configured for increasing accuracy of the blood pressure measured.

17. The extraction method of claim 15, wherein the arterial volume setpoint corresponds to a lower cuff counter pressure than a pressure corresponding to the mean arterial pressure (MAP), to improve patient comfort.

18. The extraction method of claim 15, wherein the arterial blood pressure reconstruction method uses the arterial volume signal and the cuff pressure to reconstruct an arterial blood pressure of the subject.

*    *    *    *    *